United States Patent
Blanch

(10) Patent No.: US 6,591,835 B1
(45) Date of Patent: Jul. 15, 2003

(54) PNEUMATICALLY CONTROLLED MULTIFUNCTION MEDICAL VENTILATOR

(75) Inventor: Paul B. Blanch, Alachua, FL (US)

(73) Assignee: Airon Corporation, Melbourne, FL (US)

( * ) Notice: Subject to any disclaimer, the term of this patent is extended or adjusted under 35 U.S.C. 154(b) by 0 days.

(21) Appl. No.: 09/508,706

(22) PCT Filed: Sep. 24, 1998

(86) PCT No.: PCT/US98/20059

§ 371 (c)(1),
(2), (4) Date: Mar. 15, 2000

(87) PCT Pub. No.: WO99/16491

PCT Pub. Date: Apr. 8, 1999

Related U.S. Application Data

(60) Provisional application No. 60/060,187, filed on Sep. 26, 1997.

(51) Int. Cl.[7] .............................................. A61M 16/00
(52) U.S. Cl. .............................. 128/204.25; 128/204.26
(58) Field of Search ........................ 128/204.26, 204.29, 128/205.11, 204.18, 204.21, 204.25, 204.22, 203.25, 204.24, 205.24

(56) References Cited

U.S. PATENT DOCUMENTS

| | | | | |
|---|---|---|---|---|
| 3,662,751 A | * | 5/1972 | Barkalow et al. ...... | 128/204.25 |
| 4,060,078 A | * | 11/1977 | Bird ...................... | 128/204.25 |
| 4,072,148 A | * | 2/1978 | Munson et al. ......... | 128/205.11 |
| 4,141,354 A | | 2/1979 | Ismach .................... | 128/145.6 |
| 4,197,843 A | * | 4/1980 | Bird ...................... | 128/200.14 |
| 4,340,044 A | * | 7/1982 | Levy et al. ............. | 128/204.21 |
| 4,651,731 A | * | 3/1987 | Vicenzi et al. ......... | 128/204.25 |
| 4,930,501 A | | 6/1990 | Bird ...................... | 128/204.25 |
| 5,007,420 A | * | 4/1991 | Bird ...................... | 128/200.14 |
| 5,040,529 A | * | 8/1991 | Zalkin .................... | 128/204.18 |
| 5,165,398 A | * | 11/1992 | Bird ...................... | 128/204.25 |
| 5,303,698 A | * | 4/1994 | Tobia et al. ........... | 128/204.21 |
| 5,664,563 A | * | 9/1997 | Schroeder et al. ..... | 128/204.24 |
| 5,862,802 A | * | 1/1999 | Bird ...................... | 128/204.18 |
| 6,000,396 A | * | 12/1999 | Melker et al. ......... | 128/204.21 |

* cited by examiner

*Primary Examiner*—Weilun Lo
*Assistant Examiner*—Mital Patel
(74) *Attorney, Agent, or Firm*—Allen, Dyer, Doppelt, Milbrath & Gilchrist, P.A.

(57) ABSTRACT

A multiple functionality pneumatically controlled medical ventilator provides precision regulation of tidal/forced breathing, and continuous positive airway pressure (CPAP)-based spontaneous breathing capability. The ventilator includes a patient breathing gas coupler that is adapted to be coupled to a patient airway breathing interface, and an input port to which a pressurized breathing gas is coupled, A pressure regulator supplies breathing gas at a positive pressure sufficiently higher than nominal lung pressure to prevent collapse of the patient's lungs. A tidal breathing gas supply unit periodically generates a volume-regulated tidal breathing gas for application to the patient airway breathing interface, while the CPAP valve supplies a pressure-regulated breathing gas to the patient airway breathing interface, in response to a patient demand for breathing gas that is exclusive of the tidal breathing supply.

17 Claims, 2 Drawing Sheets

PNEUMATICALLY CONTROLLED MULTIFUNCTION MEDICAL VENTILATOR

CROSS-REFERENCE TO RELATED APPLICATION

The present application claims the benefit of U.S. Provisional Patent Application Serial No. 60/060,187, filed Sep. 26, 1997, entitled: "Portable Medical Ventilator," the disclosure of which is incorporated herein.

FIELD OF THE INVENTION

The present invention relates in general to an assisted breathing device or medical ventilator that may be used in a variety of human and animal patient applications, such as, but not limited to, medical facilities (e.g., hospitals, physicians' and veterinary offices and the like), as well as medical field unit and emergency vehicle applications. The invention is particularly directed to a new and improved portable medical ventilator that provides both precision pneumatic regulation of tidal/forced breathing, and continuous positive airway pressure (CPAP)-based spontaneous breathing capability.

BACKGROUND OF THE INVENTION

Currently available portable medical ventilator units generally fall into one of two categories: i- relatively simple or limited capability pneumatically controlled units (typically carried by emergency vehicles), and ii-sophisticated electrically (both AC and battery) powered, electronically (microprocessor)-controlled systems, that are essentially comparable in function to in-house (e.g., hospital) devices. The former devices suffer from the fact that they are not much more that emergency oxygen supplies. An obvious drawback to the devices of the second category is the fact that, as electrically powered, system level pieces of equipment, they are relatively expensive and complex. Moreover, electronic systems are subject to a number of adverse influences, such as electromagnetic interference, handling abuse, and battery life-factors which do not affect a pneumatic system.

SUMMARY OF THE INVENTION

In accordance with the present invention, drawbacks of conventional medical ventilator devices such as those described above are effectively obviated by a new and improved portable, pneumatically controlled medical ventilator that provides the multiple functionality of an electronically controlled ventilator, but without the need for any electrical power (including batteries), thereby making the unit especially suited for field and emergency vehicle applications.

For this purpose, the pneumatically controlled medical ventilator of the present invention has an input port coupled to a source of pressurized gas, such as an oxygen tank carried by a medical emergency vehicle. A pneumatic link from the input port is coupled to a system-priming gas flow control switch, which is operative to prime a pneumatic timing cartridge within a pneumatic timing unit, when the ventilator is initially coupled to the oxygen source. The input port is further coupled to a system gas flow pressure regulator. The output of the system gas flow pressure regulator is coupled to an input port of a tidal breathing control switch, the operation of which controls the flow of mandatory tidal breathing gas to the patient.

The system gas flow pressure regulator provides a prescribed elevated or positive driving pressure for the mandatory tidal breathing gas supply subsystem, so that a precisely regulated amount of breathing gas may be controllably supplied to the patient. This constant positive pressure is considerably higher than the nominal lung pressure of a patient, so that it is effective to prevent collapse of the patient's lungs, and is not affected by changes in the patient's lung compliance and resistance.

The filtered breathing gas supplied is further coupled to a continuous positive airway pressure (CPAP) valve. The CPAP valve has a sensing or control port coupled to the breathing gas supply throat of a patient air supply output coupler for sensing a drop in pressure when the patient initiates or demands a breath, separate from a mandatory tidal breathing cycle. A section of breathing gas supply tubing is coupled between the patient air supply output coupler and an airway breathing interface on the patient. In response to the patient spontaneously drawing a breath, the drop in pressure in the breathing gas supply throat of the output coupler will cause the CPAP valve to couple the breathing gas (oxygen) to a gated venturi unit installed at an upstream end of the patient air supply output coupler. The venturi unit includes an ambient air input port through which filtered ambient air is drawn into the patient air supply output coupler by the flow of pressurized oxygen supplied to input port, and thereby allow a prescribed spontaneous or on-demand oxygen-enriched breathing mixture to be supplied to the patient.

An auxiliary anti-suffocation valve is coupled to the main airflow passageway of the patient air supply output coupler, to ensure that ambient air can be drawn into the main airflow passageway and supplied to the patient, in the event of a ventilator failure or depressurization of the oxygen source. Also, an overpressure valve is coupled to the main airflow passageway of the patient air supply output coupler, to prevent an excess pressure build up within the main airflow passageway of the coupler, and within the patient's lungs.

The presetable gas pressure provided at the output port of the CPAP valve is further coupled to a pneumatic conduit for inflating the diaphragm of an exhalation valve of an airway breathing interface on the patient. When a breath drawn in by the patient is patient-initiated, the pressured gas supplied by CPAP valve to the exhalation valve outlet inflates the exhalation valve's diaphragm and prevents the breathing gas in the tubing breathing gas tubing from being exhausted from the exhalation valve, and instead directed into the patient's airway, as intended. When the patient ceases inhaling, there is no longer a pressure drop in the coupler throat, causing the CPAP valve to close, and interrupt the positive pressure at the exhalation valve outlet. The exhalation valve's diaphragm thereby deflates to allow the patient to exhale.

The pneumatic timing unit supplies a periodic pneumatic control signal associated with a controllable (oxygen) concentration and rate of tidal breathing gas to a normally closed tidal breathing control switch. Tidal breathing parameters of the pneumatic control signal supplied to the pneumatic timing unit includes a pneumatic timing cartridge and a pneumatic time constant circuit for controlling the charge and bleed rates of the pressurized gas. The tidal breathing control switch receives the pressure-regulated oxygen from the system pressure regulator, and outputs a pressure-regulated oxygen to a dual position tidal air supply-mixture switch.

For a first position, the tidal air supply-mixture switch couples the pressure-regulated oxygen from the tidal breathing pneumatic circuitry to an oxygen concentration-reducing venturi, that is coupled to the output throat of the patient air supply coupler. To supply a pure (100%) oxygen breathing gas to the patient's airway breathing interface, the tidal air supply-mixture switch is turned, and thereby ported to a 100% oxygen outlet port, which is coupled through a section of oxygen supply tubing to a pure oxygen feed input port of the patient's airway breathing interface.

A manually setable, pressure regulator valve is coupled to the tidal breathing supply, and is operative to feed the exhalation valve outlet. As with the operation of the CPAP valve for an on-demand breath, this serves to inflate the exhalation valve's diaphragm, and prevent the breathing gas from being exhausted from the exhalation valve, but directed instead into the patient's airway. At the end of the tidal breath interval, the positive pressure at the output of the tidal breathing control switch is interrupted, terminating the positive pressure at the output of the pressure limit regulator valve necessary for inflating the diaphragm of the exhalation valve. The exhalation valves diaphragm deflates to allow the patient to exhale.

DETAILED DESCRIPTION

Figure 1:
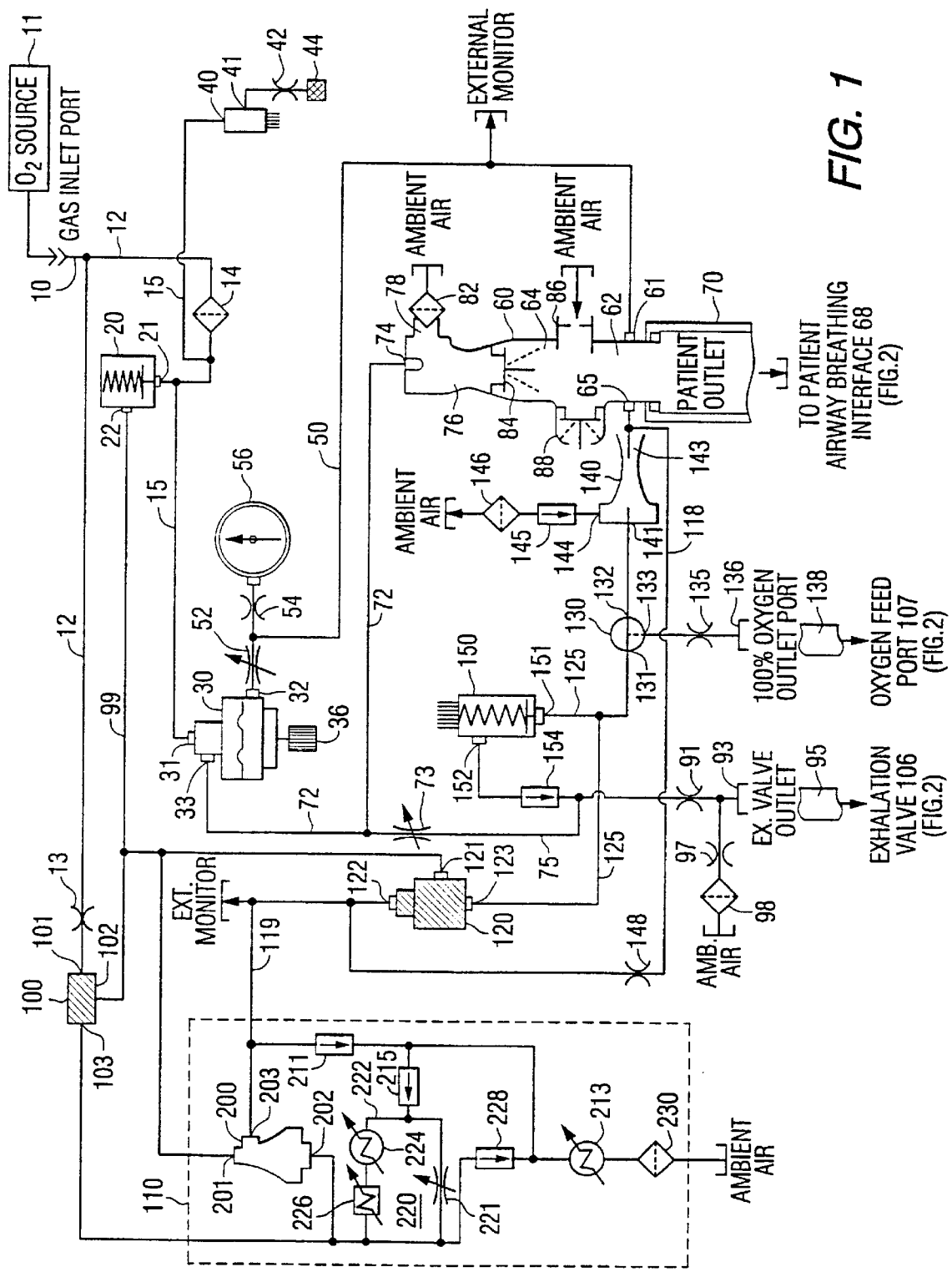
FIG. 1 diagrammatically illustrates the architecture of the medical ventilator of the present invention.

Before describing in detail the pneumatically controlled multifunction medical ventilator of the present invention, it should be observed that the invention resides primarily in what is effectively a prescribed combination of conventional pneumatic flow control and pressure regulation devices and components and interconnections therefor. As a result, for the most part, the configurations of such devices and components, and the manner in which they are interfaced with conventional breathing equipment have been illustrated in the drawings in readily understandable pneumatic flow control circuit block diagram form, which show only those specific details that are pertinent to the present invention, so as not to obscure the disclosure with details which will be readily apparent to those skilled in the art having the benefit of the description herein. Thus, the pneumatic block diagram illustrations are primarily intended to show the major components of the ventilator system in a convenient functional grouping and flow control arrangement, whereby the present invention may be more readily understood.

Referring now to FIG. 1, the architecture of the pneumatically controlled medical ventilator of the present invention is diagrammatically illustrated as comprising a patient breathing gas (oxygen) inlet port 10, to which a pressurized (e.g., within a range of 40–100 psi) source of a prescribed breathing gas (e.g., oxygen) 11 is coupled. This pressurized breathing gas source (such as a pressurized oxygen tank carried by a medical emergency vehicle) serves as a source of both (periodically metered) tidal and patient on-demand breathing gas for the patient, and to operate as a pneumatic supply for controlling the operation of the various components of the ventilator. By basing the operation of the ventilator exclusively upon mechanically and pneumatically driven components, without any need for electrical or electronic circuits, the ventilator of the invention is readily suited for the typical limited or no notice need of emergency medical personnel and eliminates any concern for the availability and or operability of batteries. All medical personnel require is a source of breathing gas (e.g., an oxygen gas tank).

A pneumatic link 12 from input port 10 is coupled directly through a flow-reducing orifice 13 to the flow control or signal input port 101 of a normally open (system-priming) gas flow control switch 100, such as an Industrial Specialties Model No. AVAP2–1032NOM. Because it is normally open, the gas flow control switch 100 provides a gas flow path for pressurized gas from the gas supply source 11 that enables a pneumatic timing cartridge 200 within a pneumatic timing unit 110, to be described, to be immediately pressurized when the ventilator is first connected to the breathing gas supply.

The pneumatic link 13 from the gas input port 10 is further coupled through an air filter 14 to a pneumatic link 15, that is coupled to an input port 21 of a system gas flow pressure regulator 20 (such as a Norgen Model No. R07–100NKA regulator, as a non-limiting example). The output port 22 of the system gas flow pressure regulator 20 is coupled through a pneumatic supply link 99 to the control port 102 of the gas flow control switch 100 and to the input port 201 of the pneumatic timing cartridge 200. It is also coupled to an input port 121 of a normally closed tidal breathing control switch 120, the operation of which controls the flow of mandatory tidal breathing gas to the patient, as will be described.

The system gas flow pressure regulator 20 serves to provide a prescribed positive driving pressure for the mandatory tidal breathing gas supply subsystem, whereby a precisely regulated amount of breathing gas may be controllably and repetitively supplied at a prescribed rate and volume to the patient. Regardless of the breathing volume of the patient (which may typically vary from 120 to 1,500 milliliters per breath) the tidal volume settings do not change.

As will be described, the oxygen content of the tidal breathing gas may be varied between pure or 100% oxygen and a relatively reduced oxygen percentage (e.g., on the order e of 60%). This constant positive pressure (e.g., on the order of 30 psi) is considerably higher than the nominal lung pressure of a patient (which is zero psi), so that it is effective to prevent collapse of the patient's lungs a not uncommon condition in ill or injured patients.

The pneumatic link 15 is further coupled to a manually adjustable low pressure alarm switch 40 (such as a Pisco Model No. RPV-⅛–10–32 F unit), the output 41 of which is coupled through a flow orifice 42 to an alarm device, such as a pneumatic whistle 44, which is activated if the input gas pressure drops below a prescribed minimum value. The filtered breathing gas supplied over the pneumatic link 15 is further coupled to an input port 31 of a continuous positive airway pressure (CPAP) valve 30, such as a Bird Products Model No. 4715 valve, as a non-limiting example. The CPAP valve 30 is operative to maintain a continuous positive pressure regardless of the patient's effort to breath. CPAP valve 30 has a patient demand pressure-monitoring or control port 32, that is coupled through a manually adjustable damping orifice 52 to a patient air supply-monitoring pneumatic link 50. Pneumatic link 50 is coupled to an on-demand breath monitoring port 61, which is coupled to the breathing gas supply throat 62 of a patient air supply output coupler 60.

To allow the pressure in the patient airway to be visually monitored by attendant medical personnel, the pneumatic link 50 is also coupled through a flow orifice 54 to an airway-monitoring pressure gauge 56. A section of hose or tubing 70 is coupled between the patient air supply output coupler 60, and an airway breathing interface on the patient, diagrammatically illustrated at 68 in FIG. 2. In addition, link 50 may be coupled to an external sensor (not shown) of an unobtrusive off-line microcontroller-based monitoring system, for monitoring the operation of the system by supervisory medical (e.g., hospital) personnel.

By 'on-demand' is meant a breath that is drawn by the patient, in addition to the 'mandatory' tidal breathing breath periodically supplied by the pneumatic timing unit 110. As a non-limiting example, this auxiliary source of breathing gas is particularly useful where medical treatment involves 'weaning' the patient off the tidal breathing supply, by gradually reducing the number of tidal breaths supplied per minute, and forcing the patient to begin to initiate more breathing on his own.

For this purpose, in response to the patient spontaneously drawing a breath (at a time other than at the occurrence of the periodic supply of a prescribed quantity of tidal breathing gas), there will be a drop in pressure in the breathing gas supply throat 62 of the output coupler 60. This drop in pressure will be coupled by the pneumatic link 50 to the patient demand pressure-monitoring port 32 of the CPAP valve 30, causing that valve to open and couple the breathing gas (oxygen) in the pressurized gas link 15 to its output port 33, at a prescribed pressure, manually setable by a valve control knob 36.

Figure 2:
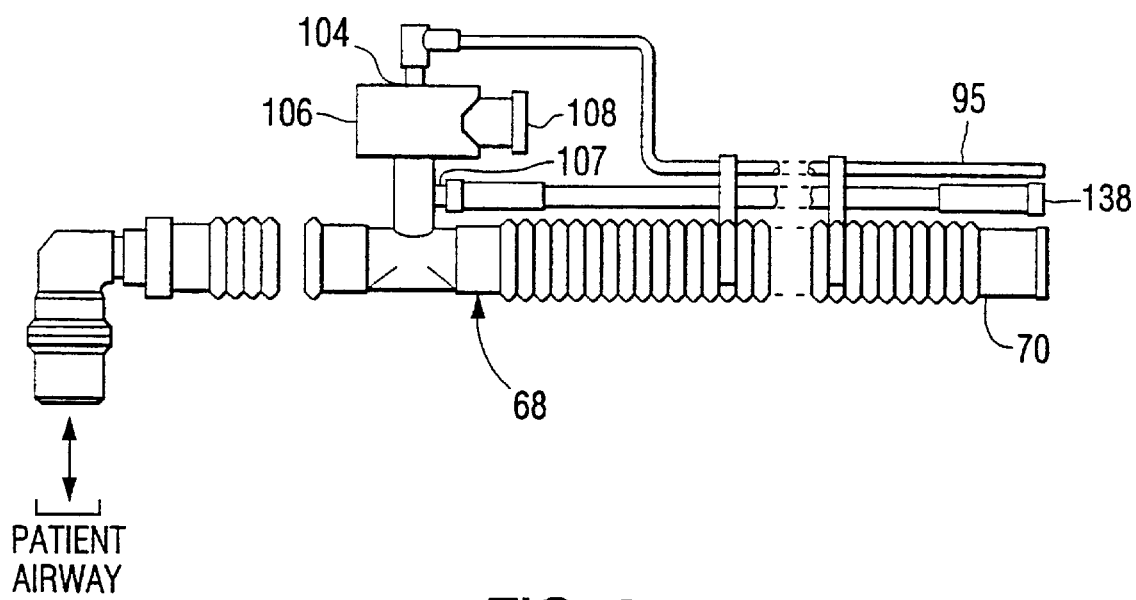
FIG. 2 diagrammatically illustrates a patient airway breathing interface to which the medical ventilator of FIG. 1 may be coupled.

The presetable gas pressure provided at the output port 33 of the CPAP valve 30 is coupled through a pneumatic link 72 and an adjustable proportioning orifice 73 to a pneumatic conduit 75 for inflating the diaphragm of an exhalation valve 106 of the patient airway breathing interface 68 of FIG. 2. CPAP output port 33 is further coupled over link 72 to an input port 74 of a gated venturi unit 76 installed at an upstream end of the patient air supply output coupler 60. As a non-limiting example, the gated venturi unit 76 may comprise a venturi unit available from Bird Products, referenced above.

The gated venturi 76 includes an ambient air input port 78 in which an air filter 82 is installed. It is through the venturi's air input port 78 that filtered ambient air is drawn into the patient air supply output coupler 60 by the flow of pressurized oxygen supplied to input port 74, to allow a prescribed spontaneous or on-demand oxygen-enriched breathing mixture to be supplied to the patient. For this purpose, the output of the gate venturi 76 is coupled (through an overpressure valve 88) into the main airflow passageway 64 of the patient air supply output coupler 60, so that a prescribed mixture of pure oxygen supplied from CPAP valve 30 and ambient air, as drawn into the venturi 76, is coupled into the throat 62 of the patient air supply output coupler 60 for delivery to the patient airway breathing interface 68.

An auxiliary anti-suffocation valve 86 (such as a Bird Product's Model No. 5536, as a non-limiting example) is coupled to the main airflow passageway 64 of the patient air supply output coupler 60. This auxiliary valve ensures that ambient air can be drawn into the main airflow passageway and supplied to the patient, in the event of a failure or depressurization of the oxygen source. As long as a positive air/oxygen flow for the patient is provided in the main airflow passageway 64 of the coupler, the anti-suffocation valve 86 remains closed, so that the air supply to the patient is controlled by the demand or tidal pneumatic control components of the invention. An overpressure or pressure limit valve 88 (such as a Halkey-Roberts Model No. 780 RPA 125, as a non-limiting example) is coupled to the main airflow passageway 64 of the patient air supply output coupler 60, to prevent an excess breathing mixture pressure build up within the main airflow passageway of the coupler 64.

As pointed out above, the output port 33 of the CPAP valve 30 is coupled through a pneumatic link 72 and a proportioning (pressure reduction) orifice 73 to pneumatic conduit 75 for inflating the diaphragm of exhalation valve 106 of patient airway breathing interface 68. For this purpose, the conduit 75 is coupled through an orifice 91 to an exhalation valve outlet 93. It is also ported to the atmosphere via a coupling orifice 97 and an air filter 98. The exhalation valve outlet 93 is coupled to a section of tubing 95 that is ported to a diaphragm inflation control port 104 of an exhalation valve 106 of the patient's breathing interface 68.

When a breath drawn in by the patient is a patient-initiated (spontaneous or on-demand) breath, to which the CPAP valve 30 responds in the manner described above, the pressured gas supplied by CPAP valve 30 (through conduit 75) to the exhalation valve outlet 93 inflates the exhalation valve's diaphragm and prevents the breathing gas in the tubing 70 from being exhausted via the output port 108 of exhalation valve 106, and instead directed into the patient's airway, as intended. When the patient ceases inhaling, there is no longer a pressure drop in the coupler throat 62 and link 50, causing the CPAP valve 30 to close. This interrupts the positive pressure at the exhalation valve outlet 93 necessary for inflating the diaphragm of the exhalation valve 106. The diaphragm thereby deflates to allow the patient to exhale though the exhalation valve.

As described briefly above, the pneumatic timing unit 110 serves to generate a periodic pneumatic control signal associated with a controllable (oxygen) concentration and rate (e.g., in a range of from two to sixty breaths per minute) of tidal breathing gas. This tidal breathing pneumatic control signal is supplied via a pneumatic link 119 to a control port 122 of the normally closed tidal breathing control switch 120. (As a non-limiting example, tidal breathing control switch flow 120 may comprise a Decker Model No. 1003 flow switch.) As pointed out above, the input port 121 of the tidal breathing control switch 120 is coupled to receive the pressure-regulated oxygen supplied via pneumatic link 99 from the system pressure regulator 20. Switch 120 has an output port 123 through which the pressure-regulated oxygen flow in pneumatic link 99 is periodically coupled to a tidal breathing supply pneumatic link 125.

The tidal breathing supply pneumatic link 125 is coupled to an input port 131 of a dual position tidal air supply-mixture switch 130, such as a Norgren Model No. 5CV-022-000 air mix switch, as a non-limiting example. The tidal air supply-mixture switch 130 has a first output port 132 coupled to a first, pressurized oxygen input port 141 of a tidal oxygen/air mixture feed venturi 140, such as a Festo Model No. 9394 venturi, as a non-limiting example. The venturi 140 is controllably coupled in the breathing gas supply path to the patient when the oxygen concentration of the breathing gas is to be less than 100% (pure $O_2$). e.g., on the order of 60%, as a non-limiting example. For this purpose, venturi 140 has an output port 143 coupled to a tidal gas mixture feed port 65 installed in the output throat of the patient air supply coupler 60. The pneumatic signal input at control port 122 is reduced in pressure by an orifice 148 and enters the tidal mixture feed port 65 of the patient air supply coupler 60. This link serves to exhaust the gas signal delivered to control port 122. It may be noted that with the pressure (e.g., 35 psi) at control port 122 being higher than the pressure at tidal mixture feed port 65 (e.g., less than or equal to 1 psi), gas always flows from port 122 to port 65.

Venturi 140 has a second, ambient air input port 144 coupled through a check valve 145 and a filter 146. As in the gated venturi 76 employed for on-demand breathing, ambient air for a reduced oxygen concentration tidal breathing mixture supplied to tidal mixture feed port 65 of the patient air supply coupler 60 is drawn into the input port 144 of venturi 140 by the flow of pressurized oxygen supplied to the venturi's input port 141, so as to provide a prescribed oxygen-enriched tidal breathing air mixture to the patient.

In order to supply pure (100%) oxygen breathing gas to the patient's airway breathing interface 68 (associated with a 90° clockwise rotation of the valve relative to that shown in FIG. 1), the tidal air supply-mixture switch 130 has a second output port 133 coupled through an oxygen feed orifice 135 to a 100% oxygen outlet port 136. The pure oxygen outlet port 136 is coupled through a section of oxygen supply tubing 138 to a pure oxygen feed input port 107 of the patient's airway breathing interface 68.

A manually setable, pressure regulator valve 150 (such as an Airtrol Model No. R-900-10-W/S) has a pressure input port 151 coupled to the tidal breathing supply pneumatic link 125. An output port 152 of pressure regulator valve 150 is coupled through a check valve 154 to pneumatic supply conduit 75, that feeds the exhalation valve outlet 93. The pressure limit regulator valve 150 is operative to supply a prescribed level of exhalation valve pressurizing gas to the exhalation valve outlet 93 during a tidal breathing interval, which prevents excessive pressure build-up in the patient's lungs.

As pointed out previously, this serves to inflate the exhalation valve's diaphragm, and thereby prevents the breathing gas in the tubing 70 from being exhausted from the exhalation valve 106, but directed instead into the patient's airway, as intended. At the end of the tidal breath interval, the positive pressure at the output 123 of the tidal breathing control switch 120 is interrupted, thereby terminating the positive pressure in link 125 and at the output port 152 of pressure limit regulator valve 150 necessary for inflating the diaphragm of the exhalation valve 106. The exhalation valves diaphragm thereby deflates to allow the patient to exhale.

In order to define the (volume and timing) parameters of the tidal breathing control signal supplied to the control input 121 of the tidal breathing control switch 120, the input port 201 of the pneumatic timing cartridge 200 (such as Bird Products Model No. 6830 pneumatic timing cartridge, as a non-limiting example) of the pneumatic timing unit 110 is coupled to the pressure-regulated oxygen flow pneumatic link 99. Port 201 is used to continuously pressurize the timing cartridge 200 during repetitive tidal breathing cycles, subsequent to the initial charging of the pneumatic timing cartridge 200 via a control port 202 that is coupled to the output port 103 of the normally open gas flow control switch 100, as described above.

The pneumatic timing cartridge 200 has an output port 203 coupled to the pneumatic link 119, and through a check valve 211 to a variable pneumatic resistor element 213, and through a check valve 215 to a pneumatic timing circuit 220. The pneumatic timing circuit 220 includes a volume balance orifice 221 and a pneumatic flow time constant control path 222, that is comprised of a variable pneumatic resistor element 224 and a variable pneumatic capacitor element 226, which is charged by the output 203 of the pneumatic timing cartridge 200. A check valve 228 is coupled between the pneumatic timing circuit 220 and the variable pneumatic resistance element 213. The variable pneumatic resistor 213 provides a pressure bleed path to ambient air through an air filter/muffler 230. The tidal breathing rate and the duty cycle of a respective tidal breath interval are preset by the time constant parameters of the components of the pneumatic timing circuit 220.

In operation, regulated pressure gas enters the input port 201 of the pneumatic timing cartridge 200. Since the timing cartridge 200 is normally open, the gas immediately exits to both the flow control switch 120 and through the check valves 211 and 215 to the pneumatic timing circuit 220. As the gas flows through the timing circuit it flows through the variable resistors 224 and 221 and variable capacitor 226 and begins to meter into timing cartridge 200. As described above, the parameters of the pneumatic resistor and capacitor components of the timing circuit may be set to provide a controllable breathing rate in a range of from two to sixty breaths per minute. At the same time, this gas pressure is delivered downstream of check valve 228 through rate control variable resistor 213. Since the volume of gas transferred by the high pressure cannot escape through the rate control path fast enough (the orifice is essentially saturated), the high pressure is maintained against the check valve 228, holding it closed.

With check valve 228 held closed, absent leaks, gas entering port 202 of the timing cartridge 200 by way of the volume control components cannot escape. As a consequence, the pressure inside the 'sealed' timing chamber increases at a rate determined by the settings of the volume control variable resistors 224 and 221. The pressure continues to rise, until it reaches that required to turn off the timing cartridge 200 (e.g., between 10 and 15 psi). When the gas flow is terminated, the gas exits from the timing chamber 200 through the check valve 228 and the rate control variable resistor 213 and air filter/muffler 230 of the rate control path. Once the pressure drops low enough in its timing chamber, the timing cartridge 200 turns back on.

As will be appreciated from the foregoing description, drawbacks of conventional medical ventilator devices described above are effectively obviated by the exclusively pneumatically controlled medical ventilator of the invention. By means of a dual, regulated positive pressure, tidal/on-demand breathing gas supply architecture, that requires no electrical power (including batteries), the invention is especially suited for a variety of hospital, field and emergency vehicle applications.

While I have shown and described an embodiment in accordance with the present invention, it is to be understood that the same is not limited thereto but is susceptible to numerous changes and modifications as are known to a person skilled in the art, and I therefore do not wish to be limited to the details shown and described herein, but intend to cover all such changes and modifications as are obvious to one of ordinary skill in the art.

What is claimed is:

1. A pneumatically controlled medical ventilator apparatus comprising:
   a patient air supply output coupler that is configured to be coupled to a patient airway breathing interface;
   a breathing gas input port to which a pressurized supply of breathing gas is coupled;
   a tidal breathing gas supply unit coupled to said breathing gas input port, and being operative to periodically supply a controllable concentration of regulated volume tidal breathing gas for application to said patient airway breathing interface; and
   a continuous positive airway pressure (CPAP) valve including a valve input port and a patient demand monitoring port, the valve input port being coupled to the breathing gas input port, and said CPAP valve being operative to supply regulated pressure breathing gas to said patient air supply output coupler, in response to a patient initiating a breath;

said patient air supply output coupler including a venturi unit and an on-demand breath monitoring port connected to the patient demand monitoring port of said CPAP valve, the venturi unit also being coupled to a source of ambient air, and being operative to supply said regulated pressure breathing gas as a mixture of ambient air and said pressurized breathing gas.

2. A pneumatically controlled medical ventilator apparatus according to claim 1, wherein said CPAP valve has a control port coupled to said patient air supply output coupler, and being operative to supply said regulated pressure breathing gas in response to a prescribed change in pressure of said control port.

3. A pneumatically controlled medical ventilator apparatus according to claim 1, wherein said tidal breathing gas supply unit is operative to periodically supply a controllable concentration of tidal breathing gas to said patient air supply output coupler.

4. A pneumatically controlled medical ventilator apparatus according to claim 3, wherein said tidal breathing gas supply unit includes a venturi unit coupled to a source of ambient air and to a periodically supplied quantity of regulated pressure breathing gas, and being operative to supply said controllable concentration of regulated pressure breathing gas as a mixture of ambient air and said regulated pressure breathing gas to said patient air supply output coupler.

5. A pneumatically controlled medical ventilator apparatus according to claim 1, wherein said tidal breathing gas supply unit is configured to periodically supply a first concentration of tidal breathing gas to said patient airway breathing interface.

6. A pneumatically controlled medical ventilator apparatus according to claim 5, wherein said tidal breathing gas supply unit is configured to periodically supply a second concentration of tidal breathing gas to said patient air supply output coupler.

7. A pneumatically controlled medical ventilator apparatus according to claim 1, wherein said patient airway breathing interface includes an exhalation valve, and wherein each of said tidal breathing gas supply unit and said CPAP valve is coupled to provide a regulated pressure for controlling the operation of said exhalation valve.

8. A pneumatically controlled medical ventilator apparatus according to claim 1, wherein said tidal breathing gas supply unit comprises a pneumatic timing unit and a tidal breathing control switch, said pneumatic timing unit being operative to supply a periodic pneumatic control signal associated with a prescribed supply of tidal breathing gas to the tidal breathing control switch, said tidal breathing control switch being operative to controllably couple pressure-regulated breathing gas to said patient airway breathing interface.

9. A pneumatically controlled medical ventilator apparatus according to claim 8, wherein said pneumatic timing unit includes a pneumatic timing device and a pneumatic time constant circuit coupled therewith for controlling charging and bleeding of pressurized gas with respect to said pneumatic timing device, and thereby defining a tidal breathing rate and a duty cycle of a respective tidal breath interval of a periodically supplied controllable concentration of regulated volume tidal breathing gas applied to said patient airway breathing interface.

10. A pneumatically controlled medical ventilator apparatus comprising a patient breathing gas output adapted to be coupled to a patient airway breathing interface applied to a patient, a breathing gas input port to which a pressurized breathing gas is coupled, a gas pressure regulator coupled to said breathing gas input port, and being operative to supply said breathing gas at a prescribed positive pressure higher than the nominal lung pressure of said patient, that is effective to prevent collapse of the patient's lungs, a tidal breathing gas supply unit coupled to said gas pressure regulator, and being operative to periodically generate a volume-regulated tidal breathing gas for application to said patient airway breathing interface, and a continuous positive airway pressure (CPAP) valve including a valve input port and a patient demand monitoring port, the valve input port being coupled to the breathing gas input port, and said CPAP valve being operative to supply pressure-regulated breathing gas to said patient breathing gas output in response to a patient demand for breathing gas, said patient breathing gas output including a venturi unit and an on-demand breath monitoring port connected to the patient demand monitoring port of said CPAP valve, the venturi unit also being coupled to a source of ambient air, and is operative to supply said regulated pressure breathing gas as a mixture of said ambient air and said pressurized breathing gas in response to a prescribed change in pressure of said patient demand monitoring port.

11. A pneumatically controlled medical ventilator apparatus according to claim 10, wherein said tidal breathing gas supply unit is operative to periodically supply a first concentration of tidal breathing gas to said patient airway breathing interface, and a reduced concentration of tidal breathing gas to said patient breathing gas output.

12. A pneumatically controlled medical ventilator apparatus according to claim 11, wherein said tidal breathing gas supply unit includes a venturi unit coupled to a source of ambient air and to a periodically supplied quantity of pressure-regulated breathing gas, and being operative to supply said reduced controllable concentration of breathing gas as a mixture of said ambient air and said pressure-regulated breathing gas to said patient breathing gas output.

13. A pneumatically controlled medical ventilator apparatus according to claim 10, wherein said patient airway breathing interface includes an exhalation valve, and wherein each of said tidal breathing gas supply unit and said CPAP valve is coupled to provide a regulated pressure for controlling the operation of said exhalation valve.

14. A pneumatically controlled medical ventilator apparatus according to claim 10, wherein said tidal breathing gas supply unit comprises a pneumatic timing unit and a tidal breathing control switch, said pneumatic timing unit being operative to supply a periodic pneumatic control signal associated with a prescribed supply of tidal breathing gas to the tidal breathing control switch, said tidal breathing control switch being operative to controllably couple pressure-regulated breathing gas to said patient airway breathing interface.

15. A method of providing a patient breathing gas to a patient airway breathing interface of a patient, comprising the steps of:

(a) periodically pneumatically supplying a regulated pressure breathing gas, at a positive pressure higher than the nominal lung pressure of said patient and effective to prevent collapse of the patient's lungs, to said patient airway breathing interface; and (b) in response to a pneumatically based patient demand for breathing gas, and exclusive of said periodic pneumatic supply of a tidal breathing gas in step (a), pneumatically supplying a continuous positive airway pressure (CPAP) breathing gas to said patient airway breathing interface through a venturi unit as a mixture of ambient air and pressurized breathing gas.

16. A method according to claim 15, wherein step (a) comprises selectively periodically supplying one of a first concentration of tidal breathing gas to said patient airway breathing interface, and a second, reduced concentration of tidal breathing gas to said patient airway breathing interface.

17. A method according to claim 15, wherein said patient airway breathing interface includes an exhalation valve, and wherein each of steps (a) and (b) comprises providing a regulated pressure for controlling the operation of said exhalation valve.

* * * * *